(12) United States Patent
Haghiri et al.

(10) Patent No.: US 12,239,771 B2
(45) Date of Patent: Mar. 4, 2025

(54) MICROFLUIDIC GAS EXCHANGE DEVICES AND METHODS FOR MAKING SAME

(71) Applicants: Centre National de la Recherche Scientifique, Paris (FR); UNIVERSITE PARIS-SACLAY, Saint-Aubin (FR)

(72) Inventors: Anne-Marie Haghiri, Sceaux (FR); Lyas Djeghlaf, Massy (FR); Julie Lachaux, Saint-Maur (FR); Alisier Paris, Malakoff (FR); Gilgueng Hwang, Gif-Sur-Yvette (FR)

(73) Assignees: Centre National de la Recherche Scientifique, Paris (FR); UNIVERSITE PARIS-SACLAY

( * ) Notice: Subject to any disclaimer, the term of this patent is extended or adjusted under 35 U.S.C. 154(b) by 817 days.

(21) Appl. No.: 17/286,947

(22) PCT Filed: Oct. 25, 2019

(86) PCT No.: PCT/EP2019/079274
§ 371 (c)(1),
(2) Date: Apr. 20, 2021

(87) PCT Pub. No.: WO2020/089116
PCT Pub. Date: May 7, 2020

(65) Prior Publication Data
US 2021/0380920 A1    Dec. 9, 2021

(30) Foreign Application Priority Data
Oct. 29, 2018    (EP) ..................... 18306405

(51) Int. Cl.
*C12M 3/00*    (2006.01)
*A61M 1/16*    (2006.01)
(Continued)

(52) U.S. Cl.
CPC ......... *A61M 1/1698* (2013.01); *B01D 53/228* (2013.01); *B01D 63/00* (2013.01);
(Continued)

(58) Field of Classification Search
CPC ... A61M 1/1698; B01D 71/701; B01D 63/00; B01D 53/228; C12M 23/16; C12M 23/24; C12M 29/04
(Continued)

(56) References Cited

U.S. PATENT DOCUMENTS 4,176,069 A    11/1979 Metz et al.
4,269,712 A    5/1981 Hornby et al.
(Continued)

FOREIGN PATENT DOCUMENTS

CN    103180032 A    6/2013
WO    WO-2018187372 A2 * 10/2018 ............. A61M 1/00

OTHER PUBLICATIONS

International Search Report issued in Application No. PCT/EP2019/079274, mailed on Feb. 7, 2020 (4 pages).
(Continued)

*Primary Examiner* — Nathan A Bowers
(74) *Attorney, Agent, or Firm* — HAUPTMAN HAM, LLP (57) ABSTRACT

Microfluidic gas exchange devices may include one or more exchange modules (100), wherein each exchange module includes: a first layer comprising: one or more primary inlets (108); a first capillary network connected to the one or more primary inlets, wherein the first capillary network extends radially outward from at least one of the one or more primary inlets, and wherein the first capillary network includes one or more injection branches (104) and a series of microchannels (106); and one or more primary outlets
(Continued)

connected to the first capillary network; and a second layer that includes a semipermeable membrane.

15 Claims, 8 Drawing Sheets

(51) Int. Cl.
- *B01D 53/22* (2006.01)
- *B01D 63/00* (2006.01)
- *B01D 71/70* (2006.01)
- *B01L 3/00* (2006.01)
- *C12M 1/00* (2006.01)
- *C12M 1/04* (2006.01)
- *C12M 3/06* (2006.01)

(52) U.S. Cl.
CPC ......... *B01D 71/701* (2022.08); *C12M 23/16* (2013.01); *C12M 23/24* (2013.01); *C12M 29/04* (2013.01)

(58) Field of Classification Search
USPC ...................................................... 435/297.1
See application file for complete search history.

(56) References Cited

U.S. PATENT DOCUMENTS

| | | | |
|---|---|---|---|
| 7,371,400 B2 | 5/2008 | Borenstein et al. | |
| 8,491,561 B2* | 7/2013 | Borenstein | A61M 1/1678 |
| | | | 436/178 |
| 8,647,410 B2 | 2/2014 | Borenstein et al. | |
| 2011/0226686 A1 | 9/2011 | Maurer | |
| 2014/0193799 A1 | 7/2014 | Borenstein et al. | |
| 2020/0061271 A1* | 2/2020 | Potkay | B01D 71/701 |

OTHER PUBLICATIONS

Written Opinion issued in International Application No. PCT/EP2019/079274, mailed on Feb. 7, 2020 (8 pages).

Gimbel, A. A. et al.; "Development of a biomimetic microfluidic oxygen transfer device;" Lab on a Chip; vol. 16; Sep. 2016; pp. 3227-3234 (9 pages).

Potkay, J. A.; "The promise of microfluidic artificial lungs;" Lab on a Chip; vol. 14; 2014; pp. 4122-4138 (17 pages).

Wagner, G. et al.; "Comment on "The promise of microfluidic artificial lungs" by J.A. Potkay, Lab Chip, 2014, 14, 4122-4138;" Lab on a Chip (4 pages).

* cited by examiner

MICROFLUIDIC GAS EXCHANGE DEVICES AND METHODS FOR MAKING SAME

FIELD OF THE INVENTION

This disclosure relates to microfluidic gas exchange devices. Particularly, the disclosure relates to the design and assembly of single and multilayer microfluidic devices, methods of making such and use thereof.

BACKGROUND OF THE INVENTION

Acute and chronic diseases of the lungs affect one of the broadest patient populations and represent some of the most urgent health care needs. Acute illnesses of the lungs include neonatal conditions related to incompletely developed lungs, severe infections, burns and other lung injuries, and Acute Respiratory Distress Syndrome (ARDS). These conditions are often treated using mechanical ventilation to sustain patient oxygen levels while the lungs recover. In intensive-care and emergency settings, gas exchange is often accomplished by mechanical ventilation. However, this method requires functioning lungs and effective treatment can be complicated in patients having decreased lung function.

Newer approaches to gas exchange include direct supplementation of blood with oxygen and removal of carbon dioxide by membrane-based exchange devices such as hollow fiber-based systems, planar or flat sheet configurations, and spiral or wound systems. These devices may include an oxygenator as the central component of the system, along with bubble traps, fluid circuitry, pumps, heat exchangers, and other components.

Other gas exchange devices incorporate microfluidic techniques to maximize surface area for air exchange, increasing efficiency and decreasing the overall design footprint. See, e.g., Gimbel et al., Development of a biomimetic microfluidic oxygen transfer device. Lab Chip, 2016, 16, 3227; Potkay, "The promise of microfluidic artificial lungs," Lab Chip, 2014, 14, 4122-4138; and Wagner et al., "Comment on "The promise of microfluidic artificial lungs" by J. A. Potkay, "Lab Chip, 2014, 14, 4122-4138."

U.S. Pat. No. 7,371,400 is directed to the microfabrication technology to form three-dimensional multilayer scaffold structures for cellular engineering of vascularized organs. The scaffolds serve as the template for cell adhesion and growth through interconnected channels in the device, which include vertically capillary networks that link successive modules into a contiguous scaffold.

U.S. Pat. No. 8,647,410 is directed to systems and methods for exchanging gas in microfabricated oxygenator device. The systems and methods relate to a device having linearly arranged microfluidic channels for blood flow separated by a semipermeable membrane from a second array of air channels configured to maximize gas exchange rates.

Published patent application WO 2018/187372 is directed to a microfluidic diffusion device that comprises a cylindrical substrate having a central axis and an outer surface, and a plurality of concentric membrane layers that extend radially outwardly from the central axis of the cylindrical substrate. At least one membrane layer is patterned to define a plurality of gas flow channels and at least one membrane layer is patterned to define a plurality of liquid flow channels to permit diffusion of gas into the liquid and/or liquid into gas.

However, despite the advancements in gas exchange devices, there remain limits on gas exchange rates; ease of manufacture, particularly for multi-channel and multi-component microfluidics; and the ability to reduce overall device size while retaining satisfactory operational efficiency.

SUMMARY

According to a first aspect, the disclosure relates to a microfluidic gas exchange device, including one or more exchange modules, wherein each exchange module includes. a first layer comprising. one or more primary inlets; a first capillary network connected to the one or more primary inlets, wherein the first capillary network extends radially outward from at least one of the one or more primary inlets, and wherein the first capillary network includes one or more injection branches and a series of microchannels, wherein said one or more injection branches are configured to divide a flow of fluid into said series of microchannels; and one or more primary outlets connected to the first capillary network; and a second layer that includes a semipermeable membrane, wherein said semipermeable membrane contacts said first capillary network and is configured to allow gas exchange with said fluid.

In a general embodiment, a first chamber is formed by said first layer enclosed by a first surface of the semipermeable membrane. Said first chamber may be configured to transport fluids. The one or more injection branches that divide the flow of fluid into said series of microchannels form a "tree structure" that enables to control pressure drop and shear forces and minimize or eliminate damage to force-sensitive components of fluids (such as proteins and cells) in the microfluidic gas exchange device.

Microfluidic gas exchange devices in accordance with present disclosure exhibit high exchange surface areas interfacing with a semipermeable membrane and minimized priming volume, enabling enhanced flow rates at low operating pressures. Microfluidic gas exchange devices may also incorporate one or more exchange modules that may be operated in parallel to increase flow rate and exchange throughput for fluids and gases processed through the device. Devices constructed in accordance with this disclosure include unique design features such as centrally located inlets that distribute fluids and/or gases axially, maximizing exchange surface area with the semipermeable membrane. In addition, capillary networks that divide the fluid flow and increase exchange surface area may include a series of microchannels that may incorporate a defined curvature that increases microchannel density and minimizes the overall device footprint.

According to one or more embodiments, microfluidic gas exchange devices may include two or more exchange modules operating in series or parallel. Parallel configurations of exchange modules may connect each exchange module inlet to a common supply line extending through the device, in addition to connecting the exchange module outlets to a common drain line. By operating in parallel, exchange modules may increase throughput, while maintaining enhanced exchange efficiency.

According to one or more embodiments, said first capillary network includes one or more injection branches of varying channel width that gradually divide said flow of fluid into said series of microchannels.

According to one or more embodiments, microfluidic gas exchange devices may include a capillary network having a series of microchannels in a parallel arrangement, where the parallel arrangement maximizes the density of microchannels interfacing with the semipermeable membrane.

According to one or more embodiments, microfluidic gas exchange devices may include a capillary network having a series of microchannels in a parallel arrangement of curved microchannels. By defining a curvature for a series of microchannels, the characteristics of flow, including pressure drop and flow uniformity, within the device may be controlled, while also decreasing the overall footprint of the exchange module. In some embodiments, the curvature of the curved microchannels may be selected such that the overall pressure in the microfluidic gas exchange device is less than or equal to 2 Pa.

According to one or more embodiments, microfluidic gas exchange devices may include a three layer structure in which the third layer includes one or more secondary inlets, and one or more secondary outlets. A second chamber may be formed by said second layer enclosed by a second surface of the semipermeable membrane that opposes the surface forming the first chamber. Said second chamber may be configured to transport gas or fluid.

In some embodiments, the third layer may also include a second capillary network that is distinct or complementary to the first capillary network. In some embodiments, the second capillary network may be designed to include two or more concentric microchannels. Concentric microchannels may be used to create a flow of fluid or gas that is transverse to the flow of fluid in the first capillary network, increasing the exchange efficiency. Secondary inlets and secondary outlets in the second capillary network may also contain one or more microchannels that control flow into and from the device.

According to one or more embodiments, microfluidic gas exchange devices may be scaled to a variety of sizes, include circular designs having a diameter of about 10 mm. In some embodiments, microfluidic gas exchange devices may have a total exchange surface area in the range of about 0.0040 m$^2$ to about 0.0050 m$^2$.

In the present description, the term "about" means the same as a margin lower and/or greater than 10%, for example 5%, of the respective value According to one or more embodiments, microfluidic gas exchange devices may include one or more layers that are constructed from the same or different materials.

According to one or more embodiments, microfluidic gas exchange devices may be oxygenation devices that are used to oxygenate blood for various medical interventions.

According to a second aspect, the disclosure is directed to methods of oxygenating blood using the microfluidic gas exchange device of the first aspect.

According to a third aspect, the disclosure is directed to methods for wet assembling a microfluidic gas exchange device, comprising: producing an exchange module by affixing a first layer to a second layer to generate a combined first layer and second layer, wherein the first layer comprises: one or more primary inlets, a first capillary network connected to the one or more primary inlets, wherein the first capillary network extends radially outward from at least one of the one or more primary inlets, and wherein the first capillary network comprises one or more injection branches and a series of microchannels, and one or more primary outlets connected to the first capillary network, wherein the second layer comprises a semipermeable membrane, and wherein affixing comprises applying a solvent mixture to at least one of the first layer or second layer.

According to one or more embodiments, methods of constructing microfluidic gas exchange devices may include affixing a third layer to the combined first layer and second layer, wherein affixing involves the application of a solvent mixture to at least one of the third layer or the combined first layer and second layer. Methods of wet assembly may also include affixing the exchange module to one or more additional exchange modules to construct multi-module devices.

DETAILED DESCRIPTION

In one aspect, embodiments of the present disclosure are directed to the design and construction of microfluidic exchange devices that utilize micropatterned capillary networks to tune various performance aspects including flow rate, pressure drop, surface-area-to-volume ratio, exchange efficiencies, and priming volumes. Microfluidic devices in accordance with the present disclosure may include one or more exchange modules having a first chamber forming a large exchange surface created by arrays microchannels that interfaces incoming fluids with a semipermeable membrane that is also in contact with a second chamber that may contain a gas or liquid that exchanges various components with the fluid in the first chamber. In another aspect, embodiments of the present disclosure are directed to microfluidic blood gas exchange devices for infusing blood with gases including oxygen, nitrogen, mixed air, and the like.

Microfluidic exchange devices in accordance with the present disclosure may include at least two chambers separated by a semipermeable membrane. Chambers within an exchange device may include microfluidic capillary networks that subdivide fluid (or gas) flow into microchannels that are formed, in part, with the surface of the semipermeable membrane. Subdivision of the fluid flow increases the overall surface area of fluid in contact with the membrane and, depending on the thickness and porosity of the membrane, increases the rate of exchange of gases, liquids, and fluid components with fluids or gases in the opposing chamber of the device.

In one or more embodiments, microfluidic exchange devices may include capillary networks of microchannels configured to provide near uniform flow and hydraulic resistance, and tunable operating pressures for compatibility with a wide variety of target applications. For many applications such as blood oxygenation, flow rate is one of the key limitations to current oxygenation devices. Blood must flow through a gas exchange device fast enough that treatment times are reasonable for the health and convenience of the patient. While volumetric flow may be increased by increasing the dimensions of the microchannels, doing so increases the diffusion length from the membrane surface, and reduces the efficiency of exchange. In addition, increasing flow rates increases shear stress, which can damage components of a treated fluid, such as rupturing blood cells or denaturing proteins.

Another factor in gas exchange in microfluidic devices is contact time with a membrane, where increased contact time translates to increased rates of gas exchange. Other design considerations that affect gas exchange are the porosity and thickness of the exchange membrane. While thinner membranes allow faster exchange rates, thin membranes are less stable mechanically and must have some degree of support to prevent rupture. In some embodiments, microfluidic devices may have a minimal priming volume. Minimal priming volume is useful for a multitude of applications in which the fluid being treated is a finite volume, particularly for blood oxygenation applications where minimal priming volumes reduce the need for supplementation by transfusion and the like.

A simple and first-order mathematical model for the oxygen pressure ($P_{O2B}$) in an artificial lung based on microchannels was proposed by Potkay el al., Biomed. Microdevices, 2013, 15(3), 397-406. Potkay proposes a mathematical model that estimates oxygen pressure in a blood channel based on a given channel height and distance. Potkay's model highlights a number of parameters that control gas exchange in the system, including the effective gas exchange surface, the height of channel transporting the blood, and the thickness of the membrane. The relationship is described according to Eq. 1, where Q is blood flow, A is the surface area available for gas exchange, $PO2_{B,i}$ is the partial pressure in the blood inlet, $PO2_G$ is partial of oxygen in the blood supply, $PO2_{B,o}$ is the partial pressure in the blood outlet, and $S_{B,O2}$ is average effective resistance to diffusion of oxygen in a blood sample being tested.

$$Q = \frac{A}{S_{B,O2} \cdot R_{D,O2} \cdot \ln\left(\frac{PO2_{B,i} - PO2_G}{PO2_{B,0} - PO2_G}\right)} \quad (1)$$

$R_{D,O2}$ is the effective resistance to the diffusion of oxygen approximated as described by Eq. 2, where om is the thickness of the gas diffusion membrane, $P_{M,O2}$ is the permeability of the membrane to oxygen, H is the average height of the blood channel, and $D_{B,O2}$ is the effective diffusivity of oxygen in the blood sample being tested. $D_{B,O2}$ is the effective diffusivity of oxygen in the sample being tested.

$$R_{D,O2} = \frac{\delta_M}{P_{M,O2}} + \frac{H/2}{S_{B,O2} \cdot D_{B,O2}} \quad (2)$$

The relationships described in Potkay indicate that there are three important parameters that drive gas exchange in a microfluidic system of fluid flowing over a membrane: the nominal flow rate, volume of filling, and active exchange surface. The nominal flow rate of an artificial lung is defined as the maximum blood flow that allows oxygenation of blood with 70% saturation input to obtain an oxygen saturation output of 95%. The nominal flow rate is therefore a simple and direct measure of both the exchange of gas and the blood circulation capacity of an artificial oxygenator. The nominal flow rate increases for small values of channel height H and membrane thickness $\delta_M$. The priming volume is defined as the total volume of blood in contact with the porous membrane should be maximized for better oxygenation efficiency, and decreases with increasing values of H and $\delta_M$.

In a particular embodiment, microfluidic exchange devices may maximize the exchange surface A, while minimizing the height of the blood channels H and the thickness of the membrane $\delta_M$. These parameter preferences create challenges to design microfluidic devices having large networks of blood channels that are bonded with large porous, thin, and mechanically sensitive membranes. In one or more embodiments, the design criteria for exchange modules in accordance with the present disclosure may set to values of H at 30 μm and the one of SM at 10 μm, with a capillary width W of 350 μm. However, while these values are generalized for blood oxygenation applications, the overall method may be adapted to other applications by those skilled in the art using the relationships set forth in Eq. 1 and Eq. 2.

Microfluidic exchange devices in accordance with the present disclosure may have varied designs that take several of the above described features into consideration, including flow rates, shear stress, and working volumes, depending on the end application. For example, in blood oxygenation applications, exchange devices can provide biomimetic and physiologically realistic flow paths for the blood that achieve highly efficient gas exchange using micron-scale diffusion distances, large surface-area-to-volume ratios, and minimal priming volume, while operating at pressures that maintain the integrity of fluid components such as cells within the microchannels.

In one or more embodiments, microfluidic exchange devices may incorporate one or more exchange modules created by multiple layers of materials that form the basic structural components that include two chambers separated by a semipermeable membrane. One or more of the chambers may include a capillary network that directs fluids and/or gases into contact with the semipermeable membrane, enabling the exchange of components with the second chamber through the porous membrane.

Microfluidic exchange devices in accordance with the present disclosure may have a circular architecture in some embodiments. With particular respect to FIG. 1A, an embodiment of a circular fluid transport chamber integrated into a fluid transport chamber layer of an exchange module 100 is shown. The circular fluid transport chamber may have a 10 cm overall diameter. During operation, fluid is driven through one or more primary inlets 108, into a capillary network that extends radially outward. With particular respect to FIGS. 1B and 1C, the capillary network includes one or more injection branches 104 of varying channel width that direct flow into a series of microchannels 106, which includes curved microchannels in some embodiments. As used herein, a "series" refers to an arrangement of two or more microchannels. Turning back to FIG. 1A, injected fluids are collected from the series of microchannels 106 following gas exchange in one or more primary outlets 110 that carry the fluid out of the exchange module. In one or more embodiments, the microchannels 106 may drain fluids into a common drain 112, prior to moving to one or more primary outlets 110.

Microfluidic devices in accordance may include one or more exchange modules arranged in series or parallel to form multilayer networks that enhance exchange rates and volume output. Exchange modules in accordance with the present disclosure may have a large volume with high surface area in a relatively small footprint, which provides increased exchange efficiency.

Capillary Networks

In general, the capillary network may be designed to optimize exchange of gases, fluids, and/or components of treated fluids through a semipermeable membrane between the chambers of an exchange device. Fluid transport chambers in accordance with the present disclosure may include one or more injection branches that function to divide fluid flow in a gradual fashion that controls pressure drop and shear forces to minimize or eliminate damage to force-sensitive components of fluids (such as proteins and cells) in the microfluidic device. The flow channels may be dimensioned to perform according to the intended application, including intended operating pressure, membrane thickness, and the nature of the fluids or gases being exchanged. Optimization may occur by modifying physical properties of the capillary network such as channel height, width, length, curvature, number, and arrangement of one or more inlets, outlets and branching points.

In one or more embodiments, capillary network architecture may be based on: (1) a centralized inlet based on Murray's law for the injection branches, and (2) a curved network of microchannels to increase the surface exchange area contacting the semipermeable membrane. Structuring capillary networks as injection branches may provide uniform distribution of the flow inside the capillaries as well as reduction of shear stress at each connection.

The geometrical configurations of vessels found in mammalian cardiovascular and respiratory systems have evolved to an optimum arrangement that minimizes the amount of biological work required to operate and maintain the system. The most distinctive feature of biological distribution systems is their hierarchical structure and the successive division of vessels (branching), which become smaller, both in length and diameter. The relationship between the diameter of the parent and daughter vessels was first derived in Murray, Proc. Nat. Acad. Sc., 1926, 12, 207, which describes the optimum relation between the diameter of the parent vessel ($d_0$) and the two daughter branches ($d_{1a}$ and $d_{1b}$) may be written as $d_0^3 = d_{1a}^3 + d_{1b}^3$. An expression known as Murray's law.

In one or more embodiments, microfluidic exchange devices may incorporate a centered injection branched structure that distributes fluid flow axially through one or more injection branches and a number of microchannels, which may number up to 256 or greater. In some embodiments, the width of each circular injection branch may be selected based on Murray's law in order to obtain 200 μm for the width of the smallest capillaries. For example, setting microchannel/capillary width to 200 μm gives W=$d_5$=200 μm–N=5 in the tree structure with $d_4$=316 μm; $d_3$=453 μm, $d_2$=921 μm; and $d_1$=1535 μm.

Flow chambers in accordance with the present disclosure may also include a series of microchannels that are curved to enhance the gas exchange surface area. In one or more embodiments, the curvature of the microchannels may be defined by a radius and may be varied to increase the channel length. For example, without changing the global architecture, a simple curvature radius of about 17 mm may increase the channel length to about 35 mm over a corresponding straight channel length of about 24 mm for the same footprint.

Figure 2:
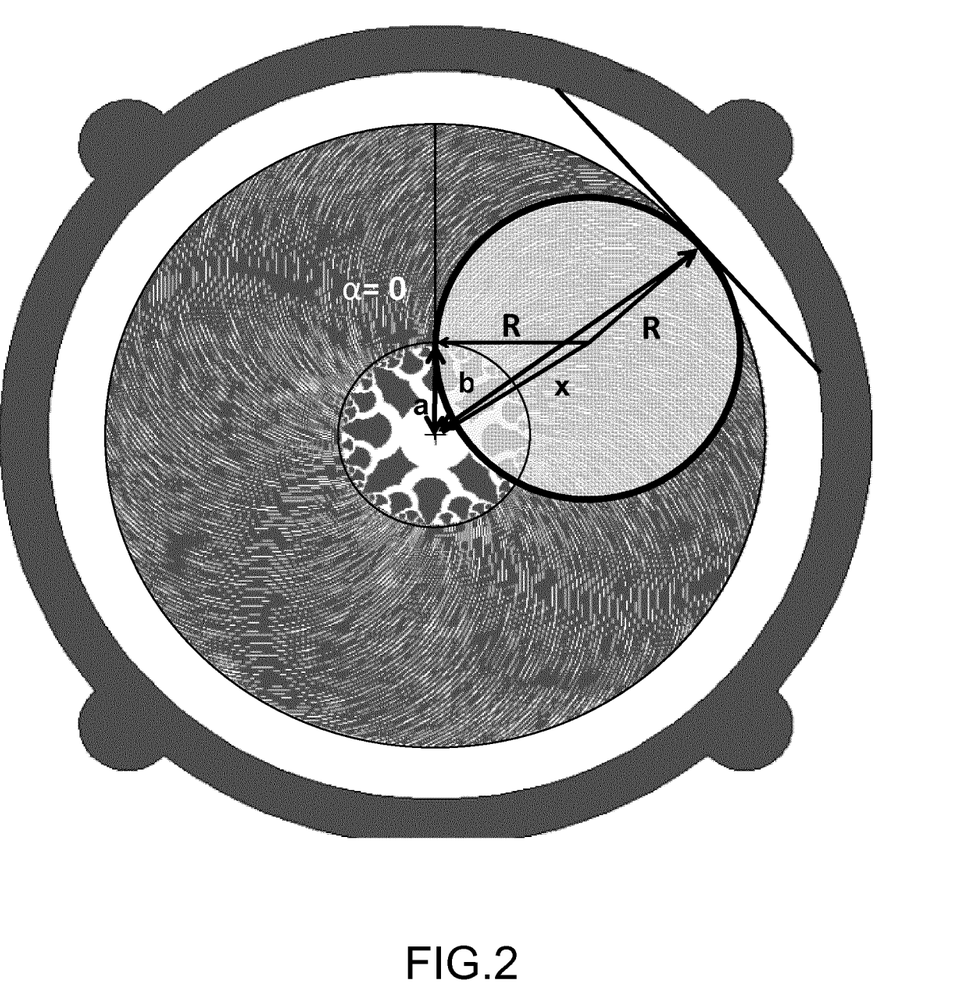
FIG. 2 is a schematic illustrating the design of curved capillary networks in accordance with embodiments of the present disclosure.

With particular respect to FIG. 2, a schematic is shown for an embodiment of a microfluidic device, highlighting micropatterning design parameters for microchannels within the fluid transport chamber, where a is the radius of the entire capillary network, a is the radius of the inlet channels, b is the total radius of the total exchange surface, and R is the curvature radius of the microchannels. In embodiments directed to 4 inch diameter circular exchange modules, the curvature radius R of the microchannels may be about 17 mm or greater, and microchannel lengths in the range of about 24 mm to about 35 mm.

Microfluidic exchange devices in accordance with the present disclosure may also be designed to control pressure drop ΔP, particularly for physiological applications where increased shear stress caused by rapid pressure changes may damage components within a biological fluid. In some embodiments, ΔP may be less than or equal to 10.6 kPa (80 mmHg) In order to manage ΔP, capillary networks may control the step down and step up in channel size, such as by adjusting the geometry of the flow chambers by micropatterning.

Pressure drop ΔP is proportional to capillary length L, and ΔP in a microfluidic device may be approximated by Eq. 3, where μ is the fluid viscosity in Pa·s, L is the channel length in m, W is the channel width in m, $H^3$ is the cubic height of the channel, and Q is the fluid flow in $m^3$/s.

$$\Delta P = 12\mu[L/WH^3]Q \quad (3)$$

Using Eq. 3, geometric parameters for microfluidic devices may be surveyed. In a particular example, a pressure drop ΔP=11.5 kPa (86 mmHg) is obtained for a 4 inch circular diameter exchange module when microchannels are designed with=5.5 cm, W=200 μm, H=35 μm, μ=0.0045 Pa·s (standard viscosity of human blood), at a flow rate Q=0.5 mL/min. In addition, because ΔP is inversely proportional to W, ΔP could be also be modified by adjusting W up to 400 μm or even 600 μm.

While Eq. 3 provides only approximated values, similar results are obtained by flow simulations using COMSOL Multiphysics® simulations to model a flow chamber having 32 rectilinear capillaries that have similar length to those capillaries used in exchange modules in accordance with the present disclosure, shear stress r is estimated to be around 4.5 Pa, which is a regime considered acceptable for many physiological applications. Simulations were performed for two cases: a "symmetric" arrangement in which fluids enter and exit by symmetrical injection branches after travelling through the 32 rectilinear capillaries; and an "asymmetric" arrangement in which fluids enter by a injection branch and feed into the 32 rectilinear categories to a collection trough. At small flow rate Q=0.016 mL/min, the pressure drop ΔP is estimated to be about 48.5% of the average P of 4.12 kPa, namely ΔP=2 kPa (15 mmHg). For a higher flow rate Q=0.5 mL/min, ΔP=62.5 kPa (468 mmHg). Simulations at higher flow rate values have to be performed with COMSOL to confirm this evolution. Results are summarized in Table 1.

TABLE 1

Summary data for COSMOL simulations

|  | Symmetric | Asymmetric |
| --- | --- | --- |
| Average Pressure (kPa) | 4.95 | 4.12 |
| Loss | 38% | 48.5% |
| Average Flux (mL/m) | 0.013 | 0.016 |
| Total Flux (mL/m) | 0.416 | 0.516 |
| Shear Stress (Pa) | 3.8 | 4.5 |

Based on these initial findings, symmetric architectures having both inlet and outlet the tree structures decrease the effective curved microchannel lengths and oxygenation flux due to the reduced exchange surface area. On the other hand, asymmetric designs having a single tree structure in the inlet provide an increase the surface area of oxygen exchange relative to the symmetric design with only a marginal increase in shear stress and pressure drop. Thus, asymmetric designs may be preferable in situations where the minimization of device footprint is desirable.

In one or more embodiments, microfluidic exchange devices may incorporate one or more exchange modules may be designed to control pressure drop within a designated regime. For example, for applications involving proteins and/or physiological fluids, pressure drop $\Delta P$ may be maintained at below <11.5 kPa (86.2 mmHg) to prevent damage to fluid components by shear forces. For example, in embodiments directed to the treatment of blood, microfluidic devices may be designed such that the flow chamber transporting blood operates at a pressure regime that maintains the shear stress experienced by the fluid equal to or below a preset threshold, such as 2 Pa, to prevent cell lysis and other negative effects. However, depending on the application, capillary networks may be designed such that the pressure drop is higher or lower, particularly where shear forces are not a concern, such as the oxygenation or carbonation of fluids.

Microfluidic exchange devices in accordance with the present disclosure may incorporate a large surface area for exchange to maximize transfer rates through a semipermeable membrane. In one or more embodiments directed to devices constructed on 4 inch diameter circular wafers, surface areas of contact with the semipermeable membrane of up to about 0.0045 m$^2$ or greater.

Microchannels present in capillary networks in accordance with the present disclosure may have dimensions that are similar to that found in naturally occurring blood vessels and capillaries, including blood channel diameter and membrane thickness. In one or more embodiments, microchannels may have a diameter or width in a range have a lower limit selected from any one of 0.5 μm, 1 μm, and 5 μm, to an upper limit selected from any one of 10 μm, 50 μm, and 100 μm, where any lower limit may be combined with any upper limit. In one or more embodiments, the constituent layers used to form the chambers of the exchange module may be micropatterned to include microchannel walls having cross-sections that may be rectangular, triangular, round, hemispherical, or other geometries.

In one or more embodiments, fluid transport chambers may have a circular or approximately circular design. In some embodiments, the fluid transport layers and/or the corresponding exchange module may be circular having a diameter in the range of 2 to 10 inches. In some embodiments, designs may achieve in a single layer a maximal value of flow rate of 25 mL/min for a 4 inch diameter structure, as compared to existing microfluidic devices having similar flow rates in stacked devices having 10 layers.

While a number of parameters are discussed with respect to a 4 inch circular design, gas and liquid exchange efficiency and/or flow rate may be controlled by enlarging or decreasing the diameter of the circular design for a given application. Moreover, embodiments of the present disclosure may also include non-circular designs, and designs having more than one fluid inlet per exchange module arranged to distribute fluids radially away from the inlet and into a capillary network.

Capillary Networks for Gases

Microfluidic gas exchange devices in accordance with the present disclosure may include one or more chambers configured to transport gases to a semipermeable membrane surface to facilitate gas exchange with a fluid transported in an opposing chamber. In one or more embodiments, the chamber may be designed to include a number of microchannels that direct incoming gas into microchannels that provide directionality and increased interaction with a corresponding fluid capillary network. In some embodiments, gas transport chambers may include a capillary network to direct gases that may be the same (complementary) or different from an opposing chamber separated by a permeable membrane. Microfluidic gas exchange devices may be configured to operate with a number of potential gas sources including air, purified gases such as oxygen, nitrogen, carbon dioxide, and gas mixtures.

Figure 3A:
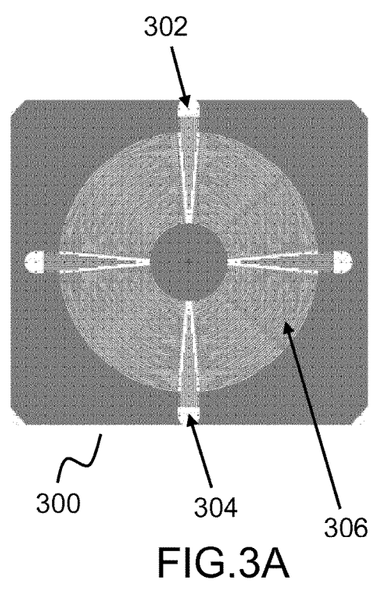
FIGS. 3A and 3B are schematics illustrating a gas capillary network for a microfluidic device in accordance with embodiments of the present disclosure.
Figure 3B:
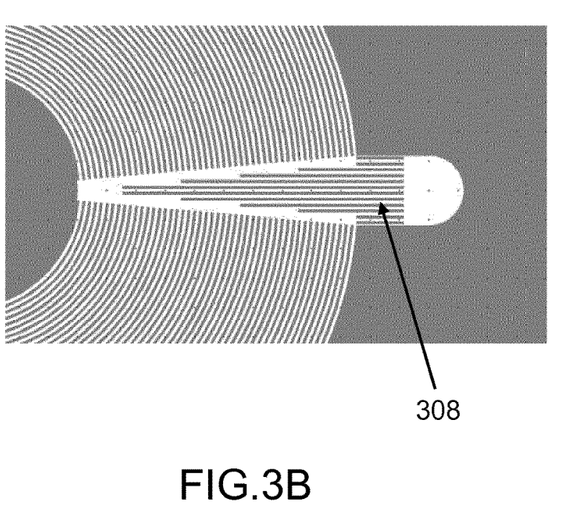

With particular respect to FIGS. 3A and 3B, an embodiment of gas capillary network integrated into a chamber of an exchange module 300 configured for gas transport is shown. Gas is driven through one or more primary inlets 302 to one or more primary outlets 304. With particular respect to FIGS. 3A and 3B, the capillary network may include an injection tree 304 having one or more microbranches of varying channel width that direct flow into a series of microchannels 306. In some embodiments, at least one of the one or more secondary inlets 302 and the one or more outlets 304 of the third layer comprises one or more microchannels 308 that direct gases or fluids into a network of microchannels, such as that shown at 306.

The microchannels may be dimensioned to perform according to the intended application. In one or more embodiments, the exchange module may have a circular footprint with a diameter of about 10 cm and an injection tree 304 having a diameter of 1 about cm.

Semipermeable Membrane

Microfluidic exchange devices in accordance with the present disclosure may be constructed with a semipermeable membrane that permits the selective exchange of gases and/or various materials between media in adjacent chambers. In one or more embodiments, a semipermeable membrane may be designed for gas to liquid exchange or liquid to liquid exchange depending on the application. For example, a semipermeable membrane may be designed such that the membrane is permeable only to gases, but is substantially impervious to fluids within a microfluidic exchange device. In another example, a semipermeable membrane may permit gases and liquids to flow through, while blocking the migration of other species depending on criteria that may include particle diameter, ionic charge, molecular weight, and the like.

Semipermeable membranes may be modified by adjusting chemical properties such as polymer composition, surface charge, hydrophobicity/hydrophilicity, and chemical functionalization; or mechanical properties such as thickness, porosity, and the like, where the rate of exchange through the membrane is dependent on the nature of the fluids and/or gases in contact with the membrane. Semipermeable membranes in accordance with the present disclosure may be prepared by any method known in the art, including spin casting, extrusion, additive manufacture, and the like. In embodiments directed to spin casting a solvent mixture of polymer in solvent may be cast into layers to produce a membrane, where the exchange rate through the membrane may be controlled by layer thickness and polymer concentration in the solvent mixture.

In one or more embodiments, semipermeable membranes may have a layer thickness that ranges from a lower limit selected from any one of 5 µm, 7 µm, 10 µm, and 20 µm to an upper limit selected from any one of 12 µm, 15 µm, 25 µm, and 30 µm, where any lower limit may be combined with any upper limit. While a number of ranges are presented, it is also envisioned that the membrane thickness may be more or less depending on the particular application.

Exchange Modules

Microfluidic gas exchange devices in accordance with the present disclosure may include one or more exchange modules assembled from multiple functional layers. In a general embodiment, an exchange module may be have the form of a trilayer structure forming a first and second chamber separated by a semipermeable membrane. The first chamber may be formed by a first layer that is enclosed by the semipermeable membrane, and may be configured to transport fluids. Similarly, the second chamber may be formed by a second layer and enclosed by a second surface of a semipermeable membrane that opposes the surface forming the first chamber, and may be configured to transport gas or liquid.

Figure 1A:
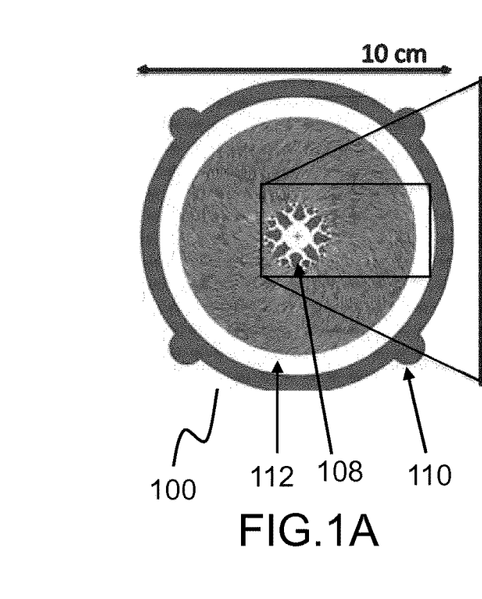
FIGS. 1A to 1C are schematics illustrating an embodiment of a fluid capillary network for a microfluidic device in accordance with embodiments of the present disclosure.
Figure 1B:
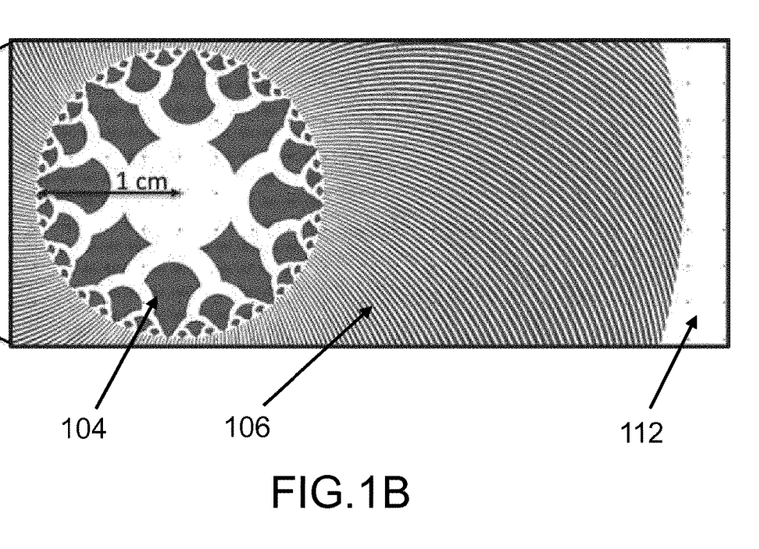
Figure 1C:
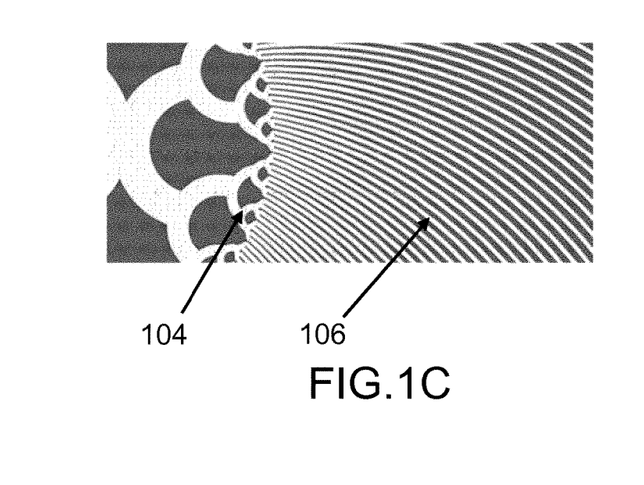
Figure 4A:
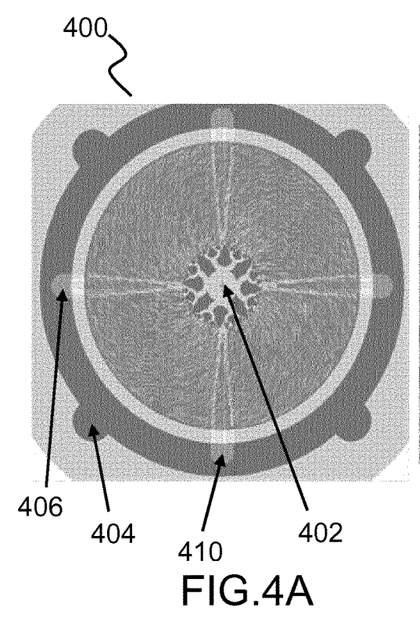
FIGS. 4A and 4B are schematics illustrating an assembled exchange module for a microfluidic device having multiple exchange modules in accordance with embodiments of the present disclosure.
Figure 4B:
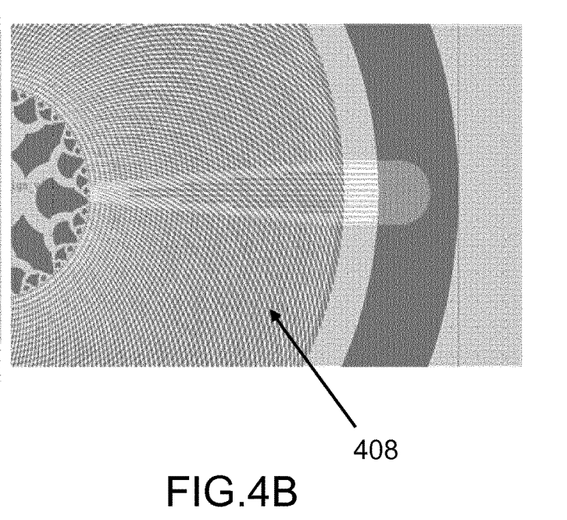

With particular respect to FIGS. 4A and 4B, a schematic is shown depicting a top-down view of an embodiment of an exchange module prepared by combining the fluid transport layer shown in FIG. 1A with a semipermeable membrane and the gas exchange layer shown in FIG. 3A. Exchange module 400 operates by injecting fluids into inlet 402, while injecting a selected exchange gas into one or more of gas inlets 406. Following gas exchange, treated fluids are collected in one or more of drains 404, while exchanged gas exits through one or more drains 410. With particular respect to 4B, an embodiment is shown in which a trilayer configuration 408 of the first and secondary capillary networks creates a perpendicular flow arrangement that enhances exchange between a fluid in the fluid transport layer and a gas in the gas exchange layer.

In one or more embodiments, fluid flow into the microfluidic exchange device and exchange modules may be initiated by gravity, external or internal pumps, capillary action, and combinations thereof.

Devices Incorporating Multiple Exchange Modules

Figure 5A:
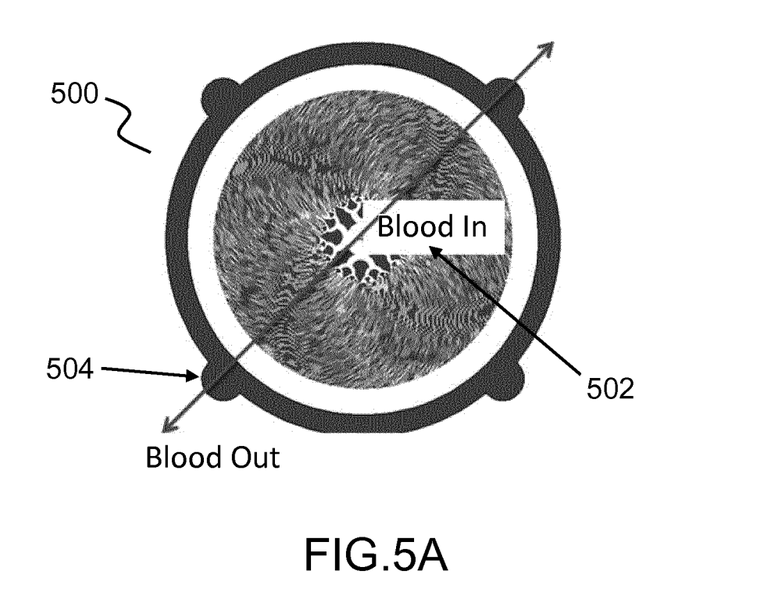
FIGS. 5A to 5D are schematics illustrating a microfluidic device having multiple exchange modules in accordance with embodiments of the present disclosure.

In addition to single exchange module design, more complicated architectures may be generated by combining multiple exchange modules in parallel or series to for extended functional arrays, which can improve efficiency as well as volume throughput and flow rate. In one or more embodiments, microfluidic devices may include one or more exchange modules unified into a single device in parallel or serial fashion. Exchange modules in accordance with the present disclosure may be combined to share a common inlet through which fluids are introduced into multiple exchange modules simultaneously (or near simultaneously). With particular respect to FIGS. 5A and 5B, the fluid transport side of a microfluidic gas exchange device 500 having multiple exchange modules is shown. FIG. 5A shows the overall fluid flow schematic in which blood (or fluid) flows into the common inlet 502 in the center of the device and, following exchange, exits the device by any one of outlets 504.

Figure 5B:
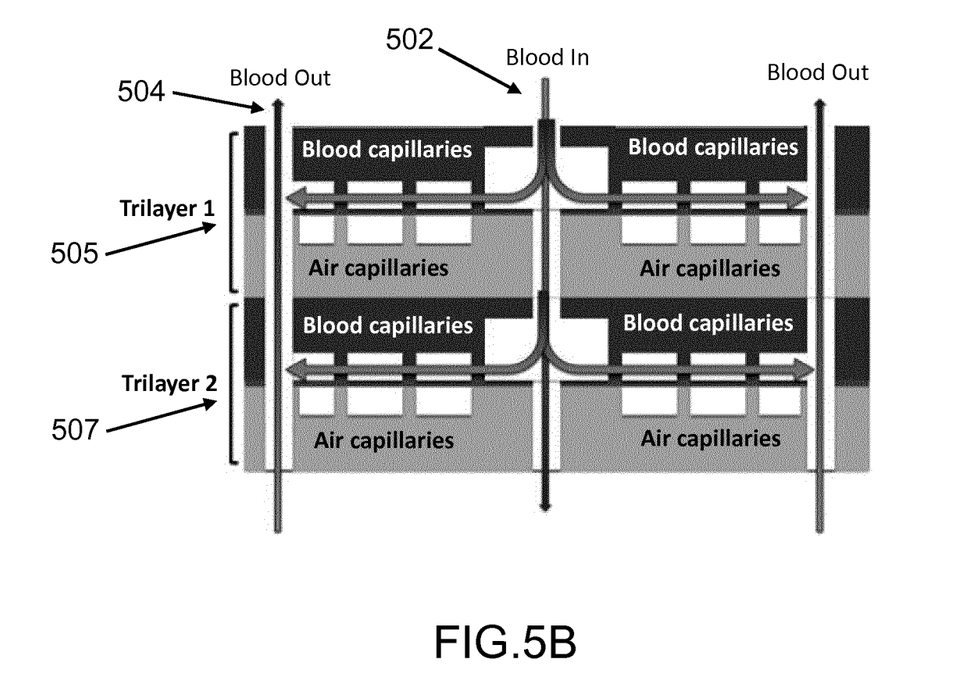
Figure 5C:
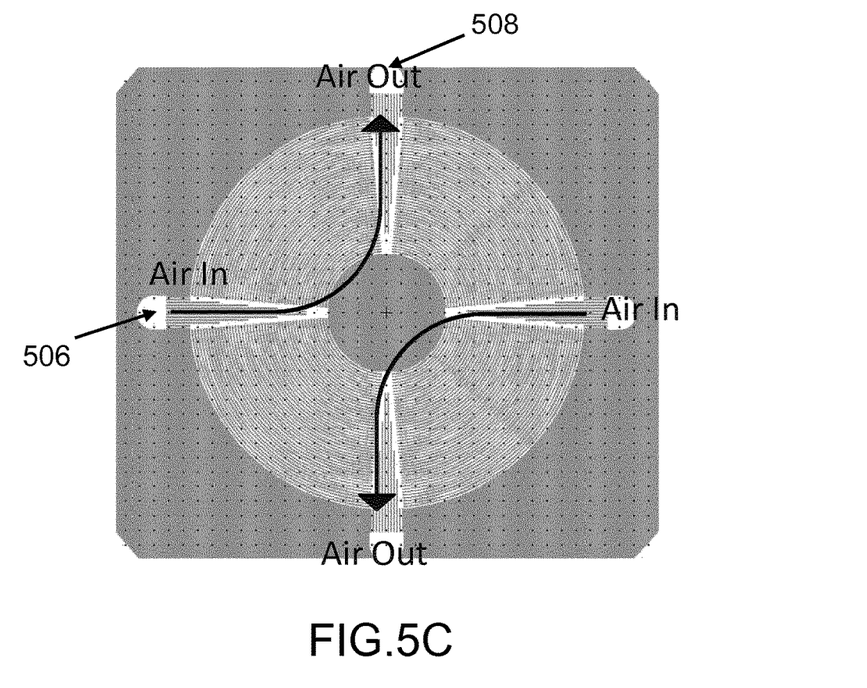
Figure 5D:
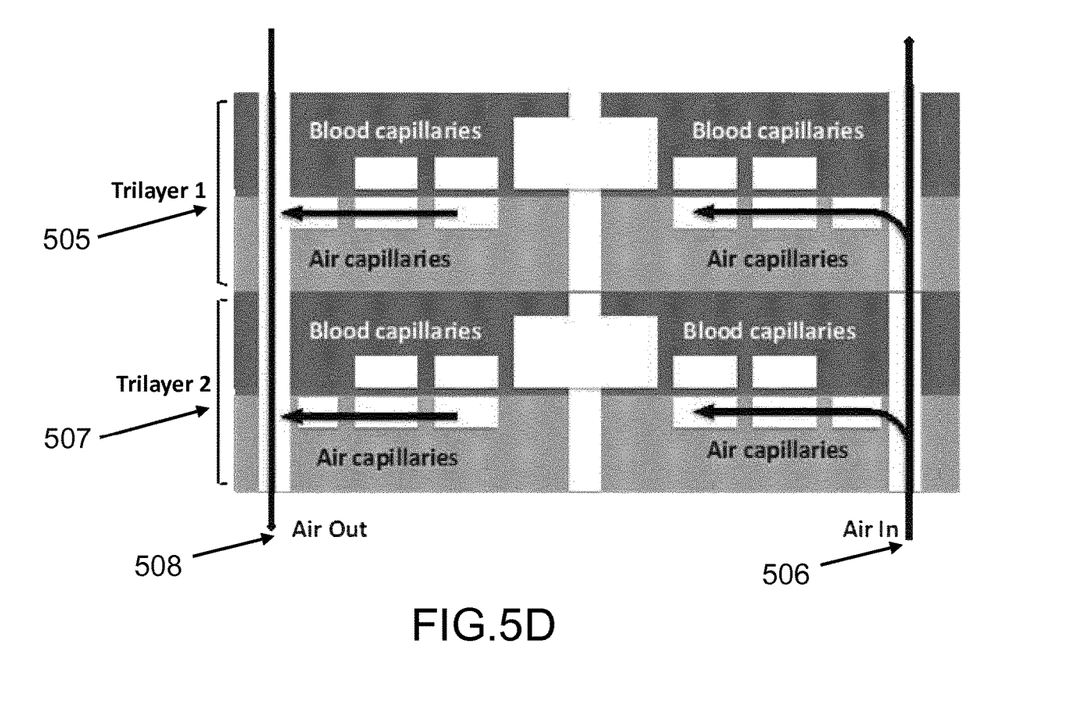
Figure 6A:
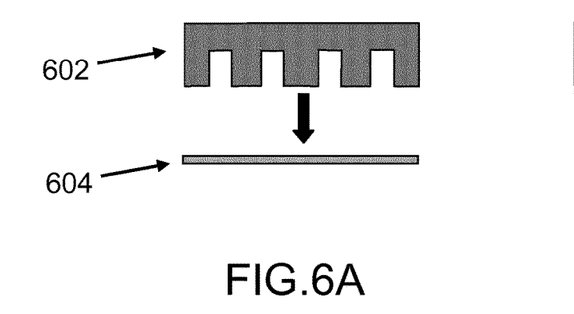
FIGS. 6A to 6D illustrate steps in an embodiment of a method of wet assembly to produce a microfluidic device in accordance with the present disclosure.
Figure 6B:
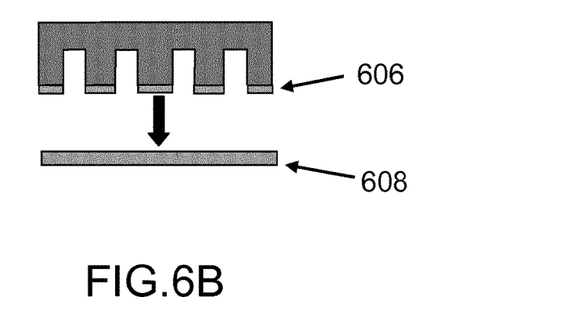
Figure 6C:
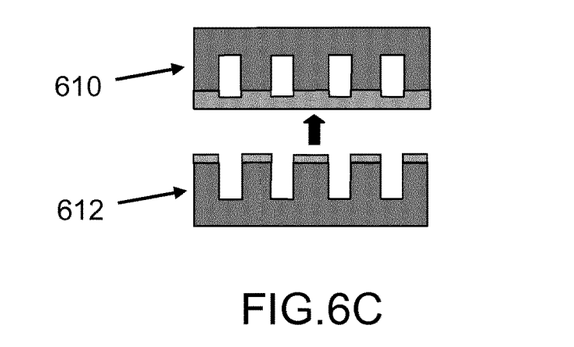
Figure 6D:
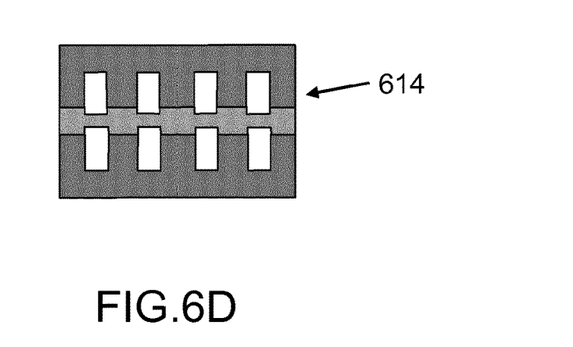

FIG. 5B is a cross-section of the microfluidic exchange device having a parallel arrangement of exchange modules. The common inlet 502 feeds into layers 505 and 507. Treated fluids are then collected into a common outlet or drain 504, which are then transported from the device. With particular respect to FIGS. 5C and 5D, the gas exchange side of a microfluidic gas exchange having multiple exchange modules is shown. With particular respect to FIG. 5C, the overall gas flow schematic in is shown flowing into one or more of inlets 506 and, following exchange and exits the device by one or more outlets 508. FIG. 5D illustrates a cross-section of the process in which incoming gas flow passes through one or more inlets 506 and layers 505 and 507, before exiting by one or more outlets 508.

In one or more embodiments, microfluidic devices directed for blood oxygenation may include parallel configurations of exchange modules that can increase flow rates to 1 L/min or greater. For example, a 4-inch circular diameter exchange module, such as that described in FIGS. 1A to 1C, may be stacked in a parallel configuration of 40 exchange modules to achieve a flow rate of 1 L/min, representing a significant improvement over previous approaches.

While a device incorporating two trilayer exchange modules is shown, more exchange modules may be incorporated. Further, while the exchange modules shown envision a design having two opposing chambers separated by a semipermeable membrane, other designs may be constructed according to the principles of the present disclosure. For example, an exchange module may be constructed in which a fluid or gas chamber is created between two semipermeable membranes, while two exchange chambers are created on the opposing sides of the membranes from the center chamber.

Polymer Materials

Microfluidic exchange devices in accordance with the present disclosure may be constructed, at least in part, from one or more polymeric materials. Polymeric materials in accordance with the present disclosure may include polymers and copolymers prepared from silicones monomers such as dimethylsiloxane, dimethylvinyl-terminated dimethylsiloxane, phenyl vinyl methyl siloxane, vinyl methyl siloxane; styrene; monomers such as alpha olefins including ethylene, propylene, butylene, and the like. In one or more embodiments, polymer materials may include siloxane polymers such s polydimethylesiloxane (PDMS); fluorosilicone polymers; polyvinylidene fluoride; polystyrene; styrene-ethylene/butadiene-styrene copolymer (SEBS), polycarbonate; polyacrylates and polymethacrylates such as polymethylmethacrylate, poly-2-methoxyethylacrylate (PMEA); cyclic olefin copolymers; polysulfone; polyurethane; biodegradable or bio compatible materials, such as polylactic-co-glycolic acid, polylactic acid, polyglycolic acid, poly[octamethylene maleate (anhydride) citrate, polyglycerol sebacate, polyoctanediol citrate, polydiol citrate, silk fibroin, polyesteramide, polycaprolactone, and the like.

In one or more embodiments, surfaces created by polymer materials may be functionalized to modify the chemical properties of channels in the device, such as improved resistance to degradation caused by materials contained in treated fluids or gases degradable coatings that reduce build-up of adsorbed species in the device, and energetic treatments that alter surface chemistry and subsequent hydrophobicity/hydrophilicity. Surface modifications specific to biological fluid-based applications may include surface-tethered compounds such as heparin that reduce clotting, and hydrophobic/hydrophilic monolayers that control protein adsorption to the device. In one or more embodiments, the inner surface of channels may be partially or completely modified.

While a limited number of embodiments are presented to demonstrate the overall concept by example, other variations on the design are possible. For example, an exchange module may be formed by placing a gas exchange layer between two semipermeable membranes on top and bottom, and placing fluid transport layers over each of the semipermeable membranes. In this way, a single gas exchange layer interfaces with two fluid transport layers. This modified exchange module may also be combined or stacked to create a multi-exchange module device as well.

Microfluidic Exchange Device Assembly

In one or more embodiments manufacture of microfluidic exchange devices may include the assembly of multiple layers to form one or more chambers for fluids and/or gases. Device layers in accordance with the present disclosure may be designed using a number of techniques including soft lithography, photoresist lift-off, additive manufacturing, and the like. Following manufacture of the constituent layers of a microfluidic device, the layers are bonded together to create one or more exchange modules.

In one or more embodiments, interlayer bonding may be performed using dry bonding assembly, wet bonding assembly, and combinations of these techniques. In one or more embodiments, microfluidic devices may be prepared by manufacturing the constituent layers separately and then assembling the layers form an exchange module or series of exchange modules using a wet assembly method to combine at least one of the layers. In some embodiments, standard assembly techniques may be used to attach layers having less complicated channel designs, where placement is less critical, and the placement error by dry techniques is within acceptable ranges. For example, for designs in which the gas transport layer has little or no internal features, dry assembly may be used to combine the layer with the exchange module, while wet bonding assembly is used to orient and attach the fluid transport layer.

In one or more embodiments, microfluidic gas exchange devices in accordance with the present disclosure may be assembled using a "wet bonding assembly" technique that allows constituent layers to assembled and adjusted prior to curing and immobilization. Wet bonding assembly methods may be contrasted with other techniques that create instant adhesion of layers during assembly, such as dry-bonding by oxygen plasma treatment in a plasma asher. Wet bonding assembly may be useful to align micropatterned layers to match up with corresponding features in neighboring layers, particularly for components having large surface area. For example, wet bonding assembly may be used to ensure that microchannels in a fluid transport layer are oriented properly with respect to channels in a gas transport layer to promote and enhance gas exchange during operations.

Wet bonding assembly in accordance with the present disclosure involves three general steps: preparation of components by applying a solvent mixture; assembly of the components; and curing the combined components. During preparation, a solvent mixture used to bond components together, may be applied to all or a subset of the components prior to assembly. Following treatment with the solvent mixture, contacting the components initiates adhesion, which cures to form a bond as the solvent in the mixture evaporates. The curing time that occurs as the solvent evaporates allows the bonding components to be aligned and repositioned, while maintaining the integrity of the final bond generated at the component interface.

During the curing step, assembled components may be heated for a period of time to evaporate the solvent component of the solvent mixture. In one or more embodiments, assembled components may be heated at an elevated temperature that is at or above the solvent evaporating temperature, which may include a curing temperature in the range of 60° C. to 70° C. In some embodiments, curing times may be in the range of 0.5 to 4 hours, but may be less or more depending on the volume and type of solvent in the solvent mixture.

With particular respect to FIGS. 6A to 6D, an embodiment of wet assembly method to manufacture a microfluidic gas exchange device is shown. Beginning at FIG. 6A, the surface of the transport layer and/or semipermeable membrane are coated with a solvent mixture, assembled, and allowed to cure. In the particular example shown in FIG. 6A, a PDMS layer 602 is treated with a solvent mixture 604 containing a dilute polymer solution of PDMS in hexane to generate the activated PDMS layer 606. In the first bonding step shown in FIG. 6B, activated PDMS layer 606 is bonded to PDMS membrane 608 by contacting the components and annealing/curing the assembly at a time and temperature appropriate for the polymer composition of the components and the solvent mixture (2 hours at 60° C.-70° C. for a solvent mixture of PDMS and hexane). In the next step shown in FIG. 6C, a second PDMS layer 612 is coated with the solvent mixture and bonded to assembled components 610. With particular respect to FIG. 6D, the fully constructed exchange module 614 is then annealed and ready for assembly in the final microfluidic exchange device.

Solvent mixtures used during wet bonding may include a mixture of one or more solvents and one or more polymers. Without being limited by any particular theory, solvent mixtures may initiate adhesion and bonding between assembled components by promoting physical crosslinks between the components and any available polymer in solution. As the solvent in the mixture evaporates, the crosslinked polymer at the interface creates a stable bond that binds the components together.

In one or more embodiments, solvents mixtures may include any solvent suitable for solubilizing the corresponding polymer component. In some embodiments, hydrophobic solvents such as normal and branched C5-C20 alkanes, aromatics such as benzene and toluene, heteroaromatics such as pyridine and derivatives, heterocycles such as dioxetane and tetrahydrofuran; halogenated solvents such as methylene chloride, chloroform, 1,2-dichloroethane, isobutyl chloride, and the like; esters such as ethyl acetate; sulfoxides such as dimethyl sulfoxide; ketones such as methylethylketone; dimethyl formamide; and the like.

In one or more embodiments, solvent mixtures may contain one or more solvated polymers. Polymers included in a solvent mixture may include homopolymers and/or copolymers. In some embodiments, polymers may include the same polymer material used to construct one or both components being assembled, or the polymer may be a different polymer type. In some embodiments, the polymer contained in a solvent mixture may be modified to include reactive groups that covalently bond with the surface of at least one of the components to be assembled.

Wet bonding assembly methods in accordance with the present disclosure may be applicable to most polymer types. In one or more embodiments, a solvent mixture may be prepared by solvating a portion of polymer corresponding to polymer constituting the components being assembled. In some embodiments, the polymer in the solvent mixture may be the same or different from the polymer constituting the components being assembled. For example, where the components are constructed from distinct polymers, the polymer in the solvent may be selected from the distinct polymers, a blend thereof, or a separate and compatible polymer type.

Wet bonding assembly may be particularly useful in cases were fabricated layers having large surface areas require minute adjustment to align micropatterns between neighboring layers or substrates. For example, while dry methods such as plasma-activated bonding require precise alignment prior to contact between layers, wet bonding assembly allows adjustment between layers during the curing window. Increased time for positioning can reduce alignment errors and wasted material, which enables the assembly of designs having larger surface area and more detailed micropatterns. For example, wet bonding assembly may allow orientation of a microfluidic network to successive layers during manufacture of an exchange module.

In one or more embodiments, wet bonding assembly may be used to create multilayer structures such as an exchange module for a microfluidic gas exchange device. In some embodiments, wet bonding assembly may also be used to construct multi-exchange module structures having two or more exchange modules connected in series or in parallel. While wet bonding assembly may be applied to the construction of microfluidic devices in accordance with the present disclosure, it is envisioned that wet assembly methods may be used to assemble other types of microfluidic devices prepared from similar materials, assembly of additive manufactured components into larger structures, and the like.

Applications

Applications for microfluidic devices in accordance with the present disclosure may include gas exchange from and to fluids, including blood oxygenation. While blood oxygenation is provided as a possible application, it is envisioned that exchange modules may be modified to handle the enrichment of any liquid that is compatible with the materials used to design the exchange module and semipermeable membrane. For example, liquids may include water or any water-based solution such as cell culture medium, physiological serum, PBS buffer solution, and the like.

Applications for microfluidic devices may also include devices for culturing microbial and eukaryotic cells, including mammalian cells, neurons, and the like; organ on-chip devices; nitrogenation, oxygenation, and carbonation of fluids.

Figure 8A:
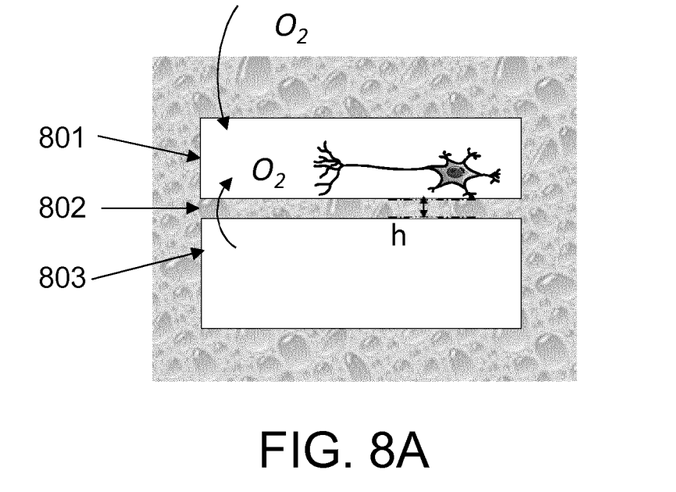
FIGS. 8A and 8B are schematics illustrating examples of microfluidic exchange devices according to the present description, configured for cell or neuron culture.
Figure 8B:
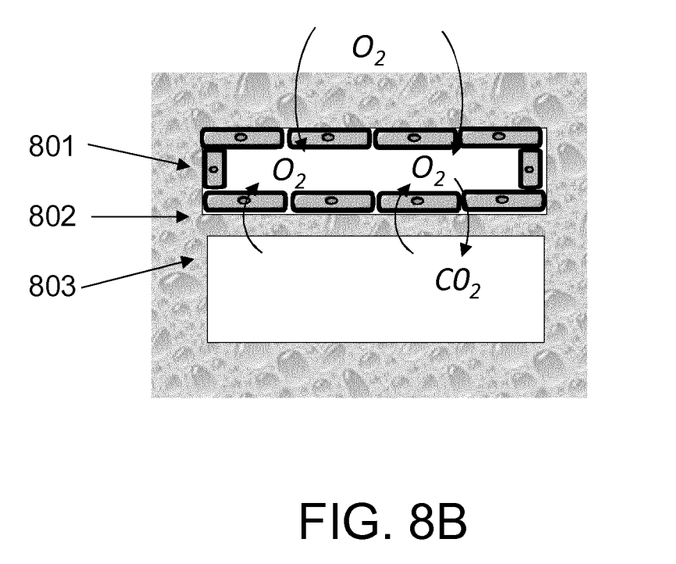

FIGS. 8A and 8B are cross-sections of examples of microfluidic exchange modules according to the present description configured respectively for cell or neuron culture. The exchange module shown in FIG. 8A or FIG. 8B has a trilayer structure, thus forming a first chamber and a second chamber (801, 803), separated by a semipermeable membrane 802 of height h, wherein h is for example equal to about 15 μm. More specifically, the first chamber 801 is formed by a first layer that is enclosed by a first surface of the semipermeable membrane 802, and is configured to transport fluids comprising neurons (FIG. 8A) or endothelial cells (FIG. 8B). Similarly, the second chamber 803 is formed by a second layer and enclosed by a second surface of the semipermeable membrane that opposes the surface forming the first chamber, and is configured to transport gas. The semipermeable membrane 802 favors longer culture of cells, neurons, and the like, with a better oxygenation all around the microfluidic exchange device where culture occurs. The wet assembly method described in FIGS. 6A to 6D may be used to manufacture such microfluidic gas exchange device dedicated to respectively cell or neuron culture.

EXAMPLES

Example 1: Wet Bonding Assembly

In this example, an exchange module is constructed using a wet bonding assembly method. The general method proceeds by (1) preparing a solvent mixture, (2) coating one or more exchange module components with the solvent mixture, (3) assembling the components, and (4) curing the assembled components.

Preparation of Solvent Mixture

In this example, a mixture of polydimethyl siloxane (PDMS) prepolymer in hexane is prepared in a 1:3 ratio. The solvent mixture was then mixed for 3 min to homogeneity. In addition, a solution of PDMS in hexane with a mass ratio of 10:1 is prepared. Solvent mixtures may be used in wet bonding assembly in addition to manufacture of semipermeable membranes.

Construction of a Semipermeable Membrane

To prepare the semipermeable membrane, a 1:3 PDMS: hexane solvent mixture was deposited on a silicon wafer using a Cee200™ spin (available from Brewer Science, Rolla, MO) rotating at a speed of 2000 rpm and an acceleration of 400 rpm/s for 30 s. Using these parameters, a thin layer of approximately 1 μm of PDMS was obtained. Calibration of the spin-coater is done based on thickness measurements using high resolution scanning electron microscopy on cross-sections of test samples. This membrane was annealed at 60° C. for 1 hour. The silicon wafer was coated to reduce adhesion to PDMS by depositing 60 μL of trichlorosilane (available from Sigma-Aldrich, St. Louis MO) in a vacuum chamber prior to spincoating.

Assembly of Exchange Module Components with Solvent Mixture

A first micropatterned PDMS layer containing a capillary network was coated in a solvent mixture and contacted with a PDMS membrane. The bonded components are then put in an oven for 1 hour at 60° C. to anneal. During the annealing step, the solvent evaporates and leaves a fine layer of PDMS at the interface of the first layer and membrane and creates an air- and fluid-tight bond. Next, a second PDMS layer was coated with the solvent mixture and assembled onto the combined first layer and membrane. The tri-layer device obtained was then placed in an oven for 1 hour at 60° C. in order to crosslink the thin layer of PDMS between the assembled components.

Example 2: Operation of a 4 Inch Microfluidic Exchange Device

Next, a comparison was made between microfluidic gas exchange devices assembled using standard oxygen plasma bonding or wet bonding assembly methods in accordance with the present disclosure. Devices surveyed were based on a 4-inch device having the complementary micropatterning for top and bottom capillary networks.

In the next example, tests were carried out with a complete tri-layer device having a fluid transport chamber micropatterned with a capillary network and a gas exchange chamber having a complementary design to the micropattern in the fluid transport chamber. The devices were assembled using the wet bonding protocol described in Example 1.

Fluidic tests were performed by injecting two different liquid dyes into each respective chamber separated by the semipermeable membrane.

Figure 7:
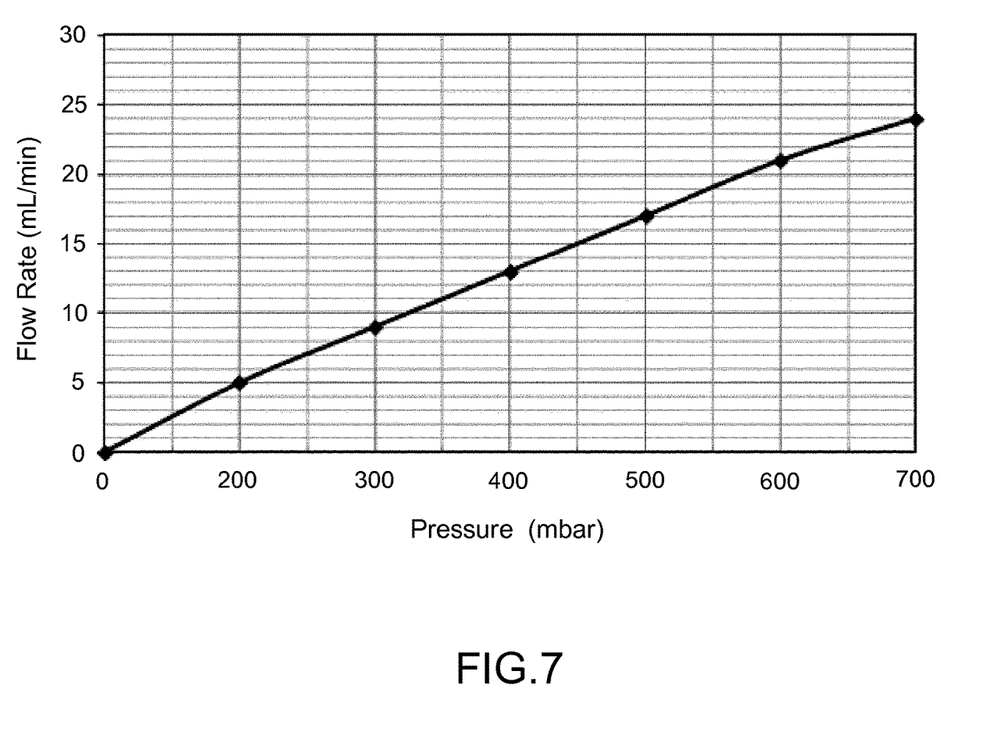
FIG. 7 is a graphical representation of flow rate as a function of pressure in a microfluidic device in accordance with the present disclosure.

In a comparison between these two methods, it is noted that the device prepared by plasma bonding did not seal properly, resulting in leaks at low pressures, while wet bonding assembly produced pressure-tight devices rated up to 1 bar or greater with independent flow rates between the fluid and gas transport chambers. In this example, the microfluidic gas exchange device constructed as described in Example 1 was capable of operation at high maximum flow values, up to 24 mL/min at a pressure of 700 mbar, indicating that the device components were securely sealed. With particular respect to FIG. 7, a graph showing flow rate as a function of pressure for a 4 inch trilayer exchange module is shown.

Next, a 4 inch microfluidic exchange device was constructed having 256 capillaries with the design of FIG. 1A and having a 25 micron thick membrane and having identical blood and air pressure levels was studied by performing a series of preliminary oxygenation experiments with venous pig blood were carried out. Oxygen ($PO_2$) and carbon dioxide ($PCO_2$) pressures in pig blood were measured using an ABL800 Flex blood gas analysis system before and after oxygenation in a microfluidic gas exchange device in accordance with the present disclosure and satisfactory oxygenation was obtained for flow rates approaching 10 mL/min.

The invention claimed is:

1. A microfluidic gas exchange device, comprising one or more exchange modules, wherein each exchange module comprises:
a first layer comprising:
one or more primary inlets;
a first capillary network connected to the one or more primary inlets, wherein the first capillary network extends radially outward from at least one of the one or more primary inlets, wherein the first capillary network comprises one or more injection branches and a series of microchannels, and wherein said one or more injection branches are configured to divide a flow of a fluid into said series of microchannels; and
one or more primary outlets connected to the first capillary network; and
a second layer comprising a semipermeable membrane, wherein said semipermeable membrane contacts said first capillary network and is configured to allow gas exchange with said fluid,
wherein the one or more primary inlets are one or more centrally located inlets that distribute fluids axially along a first direction, and
wherein the first direction of the fluids distributed axially is orthogonal to the direction of the first capillary network, wherein the first capillary network and the one or more injection branches and series of microchannels thereof extend radially outward from the primary inlets, said one or more injection branches and said series of microchannels dividing the flow of the fluid along one or more second directions each included in a plane extending perpendicularly to the first direction.

2. The microfluidic gas exchange device of claim 1, wherein the device comprises two or more exchange modules, and wherein the one or more primary inlets in the first layer of each exchange module are connected to a common supply line, and wherein the one or more primary outlets of each exchange module are connected to a common drain line.

3. The microfluidic gas exchange device of claim 1, wherein the series of microchannels of the first capillary network comprise a parallel arrangement of curved microchannels.

4. The microfluidic gas exchange device of claim 3, wherein the curvature of the curved microchannels is selected such that the pressure drop for a blood flow in the first capillary system is less than or equal to 2 Pa.

5. The microfluidic gas exchange device of claim 1, wherein each of said one or more exchange modules further comprises:
a third layer comprising:
one or more secondary inlets,
one or more secondary outlets,
a second capillary network in connection with the one or more secondary inlets and the one or more outlets, and wherein
said semipermeable membrane contacts said second capillary network.

6. The microfluidic gas exchange device of claim 5, wherein:
the second capillary network comprises two or more concentric microchannels in connection with the one or more secondary inlets and the one or more outlets.

7. The microfluidic gas exchange device of claim 5, wherein the second capillary network is complementary to the first capillary network.

8. The microfluidic gas exchange device of claim 5, wherein at least one of the one or more secondary inlets and the one or more outlets of the third layer comprises one or more microchannels.

9. The microfluidic gas exchange device of claim 5, wherein the device comprises two or more exchange modules, and wherein the one or more secondary inlets of each exchange module are connected to a common supply line, and wherein the one or more secondary outlets of each exchange module are connected to a common drain line.

10. The microfluidic gas exchange device of claim 1, wherein the exchange module has a diameter of 10 mm.

11. The microfluidic gas exchange device of claim 1, wherein the exchange module has a total exchange surface area in the range of 0.0040 $m^2$ to 0.0050 $m^2$.

12. The microfluidic gas exchange device of claim 1, wherein at least a portion of the device is constructed from one or more materials selected from a group consisting of polystyrene, polyethylene, polybutylene, styrene copolymer, polyvinylidene fluoride, polylactic-co-glycolic acid, polylactic acid, polyglycolic acid, polyoctamethylene maleate (anhydride) citrate, and polydimethyl siloxane.

13. A method for wet assembling a microfluidic gas exchange device, comprising:
producing an exchange module by affixing a first layer to a second layer to generate a combined first layer and second layer,
wherein the first layer comprises: one or more primary inlets, a first capillary network connected to the one or more primary inlets, wherein the first capillary network extends radially outward from at least one of the one or more primary inlets, wherein the first capillary network comprises one or more injection branches and a series of microchannels, and one or more primary outlets connected to the first capillary network, and wherein said one or more injection branches are configured to divide a flow of a fluid into said series of microchannels;

wherein the second layer comprises a semipermeable membrane that contacts said first capillary network, wherein affixing comprises applying a solvent mixture to at least one of the first layer or second layer, wherein the one or more primary inlets are one or more centrally located inlets that distribute fluids axially along a first direction, and wherein the first direction of the fluids distributed axially is orthogonal to the direction of the first capillary network, wherein the first capillary network and the one or more injection branches and series of microchannels thereof extend radially outward from the primary inlets, said one or more injection branches and said series of microchannels dividing the flow of the fluid along one or more second direction each included in a plane extending perpendicularly to the first direction.

14. The method of claim 13, further comprising affixing a third layer to the combined first layer and second layer, wherein affixing comprises applying the solvent mixture to at least one of the third layer or the combined first layer and second layer.

15. The method of claim 13, further comprising affixing the exchange module to one or more additional exchange modules.

* * * * *